(12) United States Patent
Saumarez

(10) Patent No.: US 10,349,852 B2
(45) Date of Patent: Jul. 16, 2019

(54) ANALYSING PHYSIOLOGICAL ELECTROGRAMS

(71) Applicant: Fen EP, Ltd., Cambridge (GB)

(72) Inventor: Richard Saumarez, Cambridge (GB)

(73) Assignee: Fen EP, Ltd., Cambridge (GB)

( * ) Notice: Subject to any disclaimer, the term of this patent is extended or adjusted under 35 U.S.C. 154(b) by 0 days.

(21) Appl. No.: 15/503,674

(22) PCT Filed: Jul. 9, 2015

(86) PCT No.: PCT/GB2015/052190
§ 371 (c)(1),
(2) Date: Feb. 13, 2017

(87) PCT Pub. No.: WO2016/024081
PCT Pub. Date: Feb. 18, 2016

(65) Prior Publication Data
US 2017/0265766 A1    Sep. 21, 2017

(30) Foreign Application Priority Data
Aug. 13, 2015 (GB) .................................. 1414330.9

(51) Int. Cl.
*A61B 5/00* (2006.01)
*A61B 5/04* (2006.01)
(Continued)

(52) U.S. Cl.
CPC ........ *A61B 5/04012* (2013.01); *A61B 5/0402* (2013.01); *A61B 5/7203* (2013.01);
(Continued)

(58) Field of Classification Search
CPC ... A61B 5/7203; A61B 5/7217; A61B 5/7246; A61B 5/04012; A61B 5/0402; A61B 5/04525
See application file for complete search history.

(56) References Cited

U.S. PATENT DOCUMENTS

| 5,172,690 A | 12/1992 | Nappholz et al. |
| 2004/0127949 A1 | 7/2004 | Kim et al. |

(Continued)

FOREIGN PATENT DOCUMENTS

| GB | 2439562 | 1/2008 |
| WO | 9625096 | 8/1996 |

OTHER PUBLICATIONS

International Search Report dated Oct. 5, 2015, and received for International Application No. PCT/GB2015/052190.
(Continued)

*Primary Examiner* — Joseph M Dietrich
(74) *Attorney, Agent, or Firm* — Fleit Gibbons Gutman Bongini Bianco PL; Jose Gutman

(57) ABSTRACT

Previous research has shown that the risk of sudden death due to cardiac arrhythmias can be predicted by observing the shape of recorded endocardial electrograms in response to pacing, and in particularly detecting certain small deflections in the recorded electrogram following early stimulation of the heart. A long standing problem has been the reliable detection of these small individual potentials because of the presence of noise in the recorded electrical signals created by other electrical equipment within a typical catheter laboratory. The solution described involves deriving a model of noise from a first portion of the electrogram in which a physiological signal is presumed to be absent, and transforming a second portion of the electrogram, presumed to contain a physiological signal, into the model of noise. The physiological signal can then be identified by identifying portions of signal within the second portion of the electrogram that do not conform to the model of noise.

20 Claims, 14 Drawing Sheets

(51) Int. Cl.
*A61B 5/0402* (2006.01)
*A61B 5/0452* (2006.01)
*A61N 1/362* (2006.01)

(52) U.S. Cl.
CPC .......... *A61B 5/7217* (2013.01); *A61B 5/7246* (2013.01); *A61B 5/04525* (2013.01); *A61B 5/7275* (2013.01); *A61N 1/3627* (2013.01)

(56) References Cited

U.S. PATENT DOCUMENTS

2005/0149134 A1 7/2005 McCabe et al.
2006/0253044 A1 11/2006 Zhang et al.

OTHER PUBLICATIONS

Written Opinion of the International Search Authority dated Oct. 5, 2015, and received for International Application No. PCT/GB2015/052190.

$$\begin{bmatrix} 1.00 & 0.87 & 0.69 & 0.55 & 0.45 & 0.37 & 0.31 & 0.27 & 0.24 & 0.22 \\ 0.87 & 1.00 & 0.91 & 0.76 & 0.63 & 0.53 & 0.45 & 0.39 & 0.35 & 0.32 \\ 0.69 & 0.91 & 1.00 & 0.94 & 0.83 & 0.72 & 0.62 & 0.55 & 0.49 & 0.45 \\ 0.55 & 0.76 & 0.94 & 1.00 & 0.96 & 0.88 & 0.79 & 0.71 & 0.65 & 0.60 \\ 0.45 & 0.63 & 0.83 & 0.96 & 1.00 & 0.97 & 0.91 & 0.84 & 0.78 & 0.73 \\ 0.37 & 0.53 & 0.72 & 0.88 & 0.97 & 1.00 & 0.98 & 0.94 & 0.89 & 0.84 \\ 0.31 & 0.45 & 0.62 & 0.79 & 0.91 & 0.98 & 1.00 & 0.99 & 0.95 & 0.92 \\ 0.27 & 0.39 & 0.55 & 0.71 & 0.84 & 0.94 & 0.99 & 1.00 & 0.99 & 0.97 \\ 0.24 & 0.35 & 0.49 & 0.65 & 0.78 & 0.89 & 0.95 & 0.99 & 1.00 & 0.99 \\ 0.22 & 0.32 & 0.45 & 0.60 & 0.73 & 0.84 & 0.92 & 0.97 & 0.99 & 1.00 \end{bmatrix}$$

ANALYSING PHYSIOLOGICAL ELECTROGRAMS

CROSS-REFERENCE TO RELATED APPLICATIONS

This application is based upon and claims priority to PCT Patent Application No. PCT/GB2015/052190 filed on 29 Jul. 2015, which is based upon and claims priority to GB Patent Application No. 1414330.9 filed on 13 Aug. 2014, the collective disclosure of which being hereby incorporated by reference in its entirety.

BACKGROUND

The present invention relates to the analysis of physiological electrograms, in particularly but not exclusively for identifying pathological cardiac conditions.

Previous research has shown that the risk of sudden death due to cardiac arrhythmias can be predicted by observing the shape of recorded endocardial electrograms in response to pacing.

The diagnostic change in electrograms consists of small deflections in the recorded electrogram following early stimulation of the heart. The heart is stimulated with apparatus that generates a stimulation sequence at one site in the heart and records electrograms from other sites within the heart.

The pacing sequence comprises of a number of stimuli at a constant rate, known as S1 stimuli. After a pre-set number of S1 stimuli an early stimulus is introduced known as the S2 stimulus or 'extra-stimulus'. The sequence is repeated. Typically the interval between S1 and S2 stimuli is reduced on each occasion until the interval is so short that the heart is no longer able to respond to the S2 stimulus.

The interval between the S2 stimulus and the following S1 stimulus is the same as the S1-S1 interval.

The predictive method depends on demonstrating that the electrogram following an extra-stimulus becomes prolonged and contains more peaks. This effect in patients that are at high risk of sudden death becomes more pronounced as the interval between the S1 and S2 stimuli is reduced.

Each individual potential of the electrogram following an extrastimulus is identified together with its delay after the extra stimulus. These data can subsequently be analyzed to predict the risk of sudden cardiac death.

A long standing problem with this method has been the reliable detection of small individual potentials within the response to an extra stimulus. This stems from the presences of noise in the recorded electrical signals that may be created by other electrical equipment within a typical catheter laboratory. The electrical noise may vary widely between different laboratories. The problem is that of reliably distinguishing between potentials in the electrogram that are of physiological origin as opposed to spurious potentials caused by electrical interference.

GB2439562 describes a method of processing date from electrograms to reduce noise. The method comprises correlating an electrogram signal with several templates to produce a correlator output associated with each template. The electrogram signal may be passed through a high pass filter beforehand.

The correlator output from trace 1 is compared with the traces produced from the other templates. The selected trace that is considered most similar is used.

A fundamental problem is that any series of templates that purport to represent a physiological signal will be correlated, and therefore the results of each correlated trace will not be independent of each other. This creates considerable difficulties in to how to combine the various correlator outputs to give optimal signal detection and avoid spurious over detection and under detection of physiological potentials within the signal.

The noise can be reduced further by identifying the peak-to-peak amplitude of the correlated output within a period of the electrogram when no physiological signal is presumed to occur. This is used to create a threshold in which any peak having an amplitude below this threshold is considered to be noise. However, signals of physiological origin may have amplitudes which are close to the threshold, as a consequence is if the threshold is set too low, the physiological derived peaks will be detected but many other peaks will also be detected due to noise. Conversely, if the amplitude threshold is too high, physiologically important features of the signal may not be detected.

BRIEF SUMMARY

An object of the invention is to overcome or at least ameliorate the above problems.

According to first aspect of the invention there is provided a method of analyzing an electrogram, for example a cardiac electrogram, to distinguish a physiological signal from noise; the method comprising:

deriving a model of noise from a first portion of the electrogram in which a physiological signal is presumed to be absent; and transforming a second portion of the electrogram, presumed to contain a physiological signal, into the model of noise, and wherein the physiological signal is identified by identifying portions of the signal that do not conform to the model of noise.

This provides an improvement over using the amplitude method because detected potentials are more likely to be genuinely physiological in origin and so subsequent analysis is greatly simplified.

In a preferred embodiment, the model of noise is derived from multiple portions of the electrogram in which a physiological signal is presumed to be absent. This provides a more accurate means of representing the noise thereby enabling improved detection of physiological signals from the noise.

It is favorable that the model of noise is derived by cross-correlation of the first portion of the electrogram in which a physiological signal is presumed to be absent with multiple templates that represent features of the presumed physiological signal to produce a number of template correlated signals.

The number and form of the templates will depend on the signal in question and can be determined by experiment. In the context of cardiac electrograms, a set of time dilated templates are used that correspond to different local conduction velocities in the region of the recording electrodes.

It is preferred that a co-variance matrix is derived from the template correlated signals for each portion of the electrogram in which a physiological signal is presumed to be absent. By deriving covariance matrices that are inherently symmetric, the eigenvectors thence derived are wholly real and orthogonal (and thus independent), and the eigenvalues are real. In this way it is possible to differentiate a signal from noise because the signal will have significant components in eigenvectors where the noise is very small or non-existent.

The method preferably comprises deriving a mean co-variance matrix from the co-variances matrices derived for each portion of the cardiac electrogram in which a physiological signal is presumed to be absent. The mean covariance matrix provides a better estimate of the behaviour of the noise throughout the entire recording.

It is preferred that the model of noise is expressed by deriving eigenvectors and eigenvalues from the mean co-variance matrix.

It is preferred that the second portion of the electrogram is correlated with multiple templates that represent features of the presumed physiological signal to produce a set of template correlated signals, and additionally favorable that a vector is derived from a first time sample of each template correlated signal of the set, and further vectors from further time samples of each template correlated signal of the set.

It is preferred that the vectors are represented as points in the model of noise by projecting each vector onto each eigenvector thereby representing the original signal as a trajectory in the model of noise, and so allows comparison of the signal and the noise.

The physiological signal is preferably identified by determining points that lie outside the limits of the model of noise thereby discriminating the signal from the noise.

The invention can also be expressed in terms of apparatus and thus according a further aspect of the invention there is provided apparatus for analyzing an electrogram to distinguish a physiological signal from noise; the apparatus comprising:

means for deriving a model of noise from a first portion of the cardiac electrogram in which a physiological signal is presumed to be absent; and means for transforming a second portion of the electrogram presumed to contain a physiological signal into the model of noise, and where the physiological signal is identified by identifying portions of the signal that do not conform to the model of noise.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIG. 6 illustrates a correlation matrix of the templates showing correlation therebetween;

DETAILED DESCRIPTION

Figure 1:
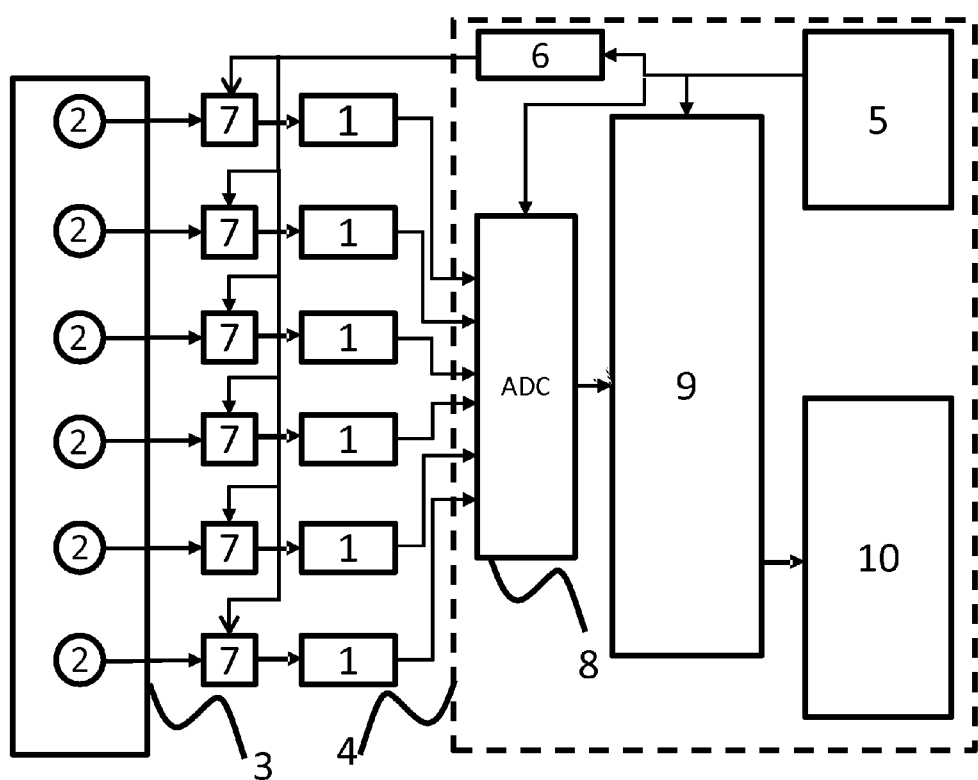
FIG. 1 is a schematic representation of apparatus for pacing a heart, recording an electrogram and subsequent analysis.

As required, detailed embodiments are disclosed herein; however, it is to be understood that the disclosed embodiments are merely examples and that the devices, systems and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any appropriately detailed structure and function. Further, the terms and phrases used herein are not intended to be limiting, but rather, to provide an understandable description. Additionally, unless otherwise specifically expressed or clearly understood from the context of use, a term as used herein describes the singular and/or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising i.e., open language. The term "coupled," as used herein, is defined as "connected," although not necessarily directly, and not necessarily mechanically. "Communicatively coupled" refers to coupling of components such that these components are able to communicate with one another through, for example, wired, wireless or other communications media. The term "communicatively coupled" or "communicatively coupling" includes, but is not limited to, communicating electronic control signals by which one element may direct or control another. The term "configured to" describes hardware, software or a combination of hardware and software that is adapted to, set up, arranged, commanded, altered, modified, built, composed, constructed, designed, or that has any combination of these characteristics to carry out a given function. The term "adapted to" describes hardware, software or a combination of hardware and software that is capable of, able to accommodate, to make, or that is suitable to carry out a given function.

The apparatus comprises amplifiers 1 that are connected to recording electrodes 2 within the heart 3 and electronics and associated software 4. A pacing and recording program 5 issues signals to a pacing signal generator 6 that is switched onto one selected electrode 2 by multiplexer 7 to stimulate the heart 3. The signals sensed by the other electrodes 2 are amplified and digitized by an ADC 8 and stored in memory 9. Subsequently the data is retrieved and analyzed by analysis program 10.

All subsequent analysis is with sampled signals, care having been taken to conform to the Nyquist sampling theorem.

The use of the multiplexer 7 allows the heart to be stimulated at different sites 3.

The functions and arrangement described above can be derived, in conjunction with the teaching within this document by the person skilled in the art.

Figure 2:
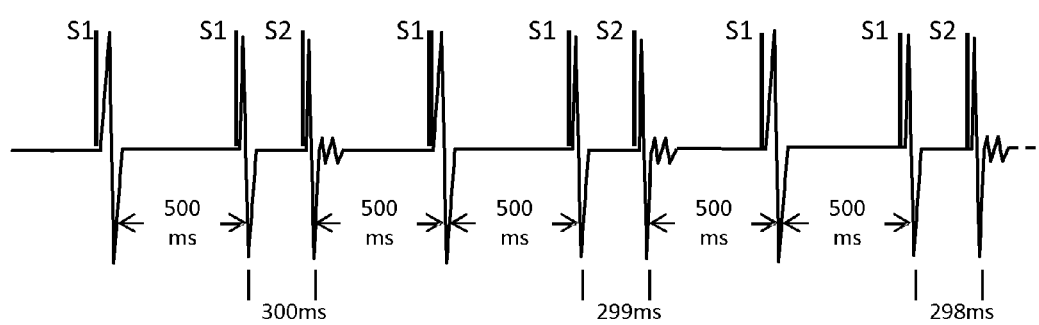
FIG. 2 is schematic representation of a paced cardiac electrogram sequence.

FIG. 2 illustrates a pacing sequence applied at one electrode 2, showing the constant rate stimuli S1 and extra-stimuli S2. The intervals between S1-S1 stimuli and the S2-S1 stimuli remain constant, in this example with an interval of 500 ms. The interval between the S1 and S2 stimuli varies, and typically reduces by one 1 ms on each occasion.

Figure 3:
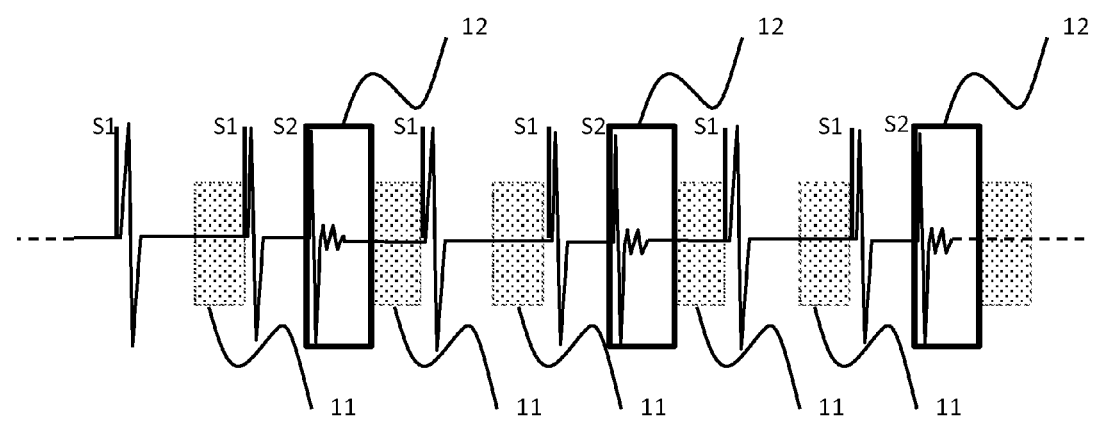
FIG. 3 is schematic representation similar to FIG. 1 illustrating the regions of the signal used to evaluate noise.

FIG. 3 illustrates the regions 11 preceding S1 stimuli that are used for evaluating noise on the premise that no physiological signals occur in these regions 11. Also shown are regions 12 that are analyzed to identify physiological signals resulting from S2 stimuli.

Figure 4:
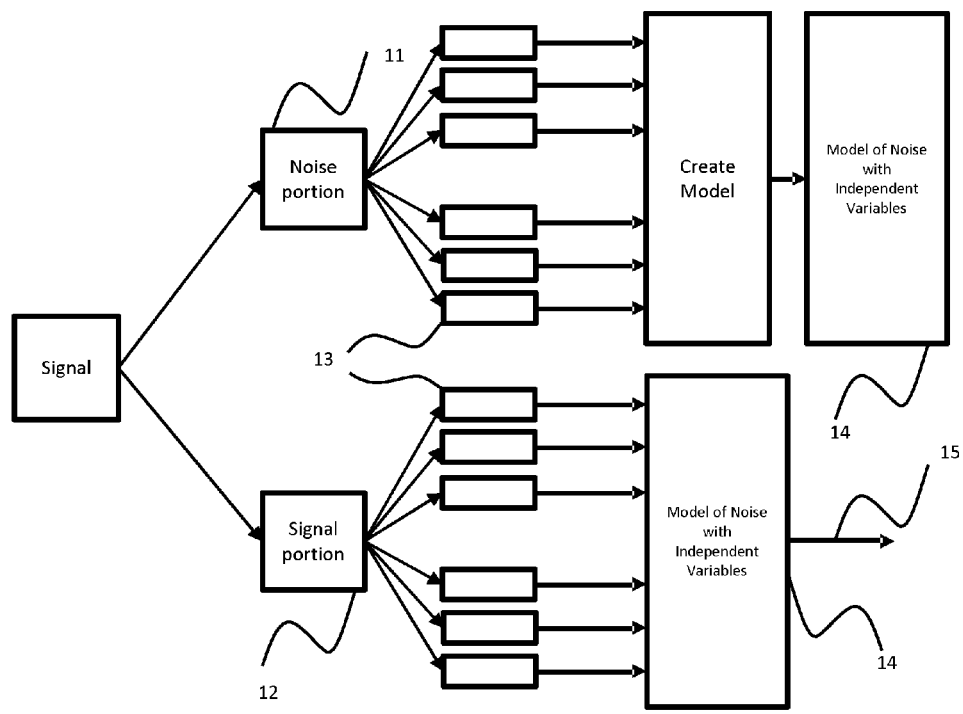
FIG. 4 is a schematic illustrating the principle of the analysis technique.

As illustrated in FIG. 4, the noise regions 11 are extracted from the recorded signal and correlated with templates 13, generated by the analysis program 10, to create a model 14 with independent eigenvectors. The templates 13 are representations of potentials of varying widths that are likely to be the result of a physiological event.

Subsequently, the portions 12 of the recorded signal are correlated to templates 13 and projected into model 14 that provides an output 15 that is indicative of whether the sample being analyzed is signal or noise.

Figure 5:
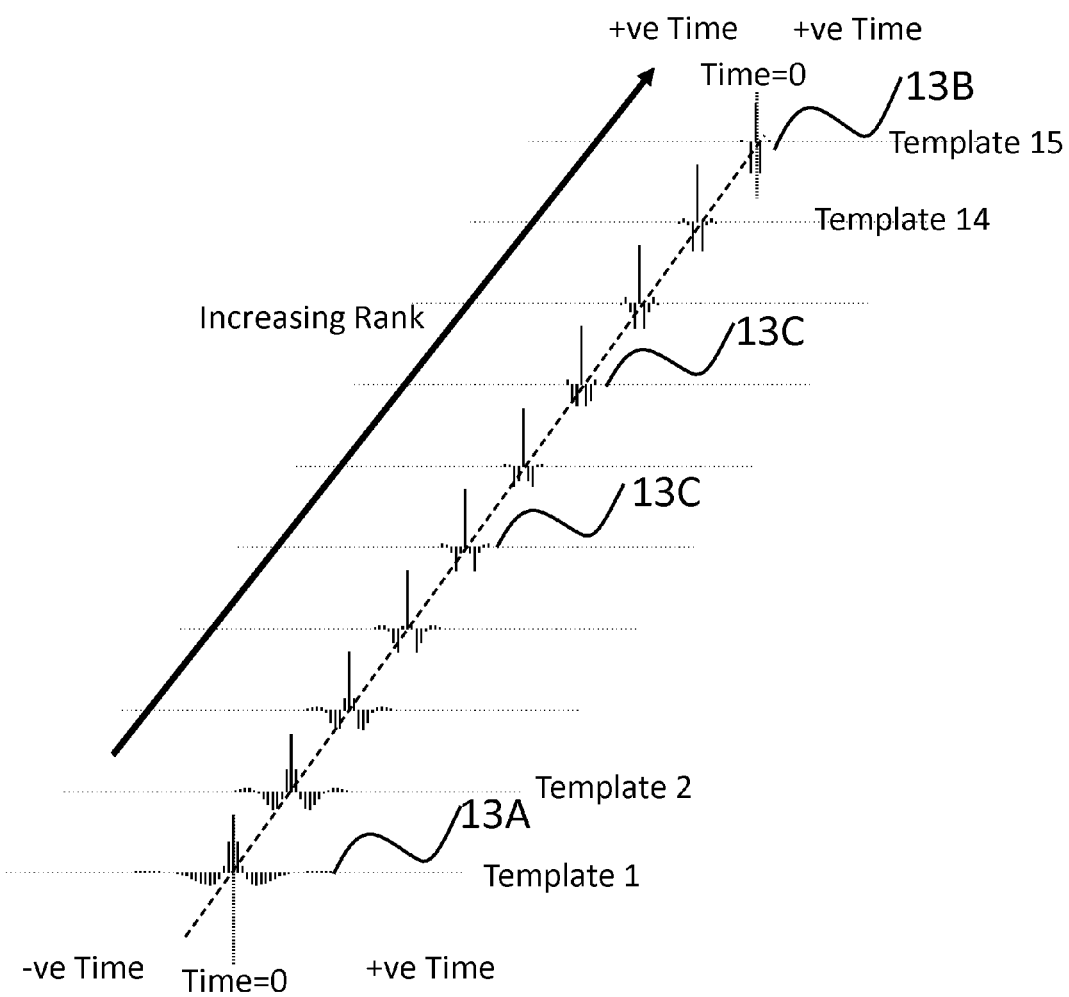
FIG. 5 is a schematic of time domain representation of the templates.

FIG. 5 illustrates the fifteen templates 13 that are correlated with the signals 11 12. Template number one 13A has the longest time duration while template number fifteen 13B has the shortest. The intermediate template numbers 13C shorten progressively.

In practice the templates are always used in their frequency domain representations, i.e. their discrete Fourier transform, for computational efficiency.

The correlation between templates 13 is shown as a correlation matrix, see FIG. 6, in which each element is the correlation between template n and template m where n and m are the template numbers. This shows that the templates 13 are not independent since if they were all non-diagonal elements would be equal to zero.

Figure 7:
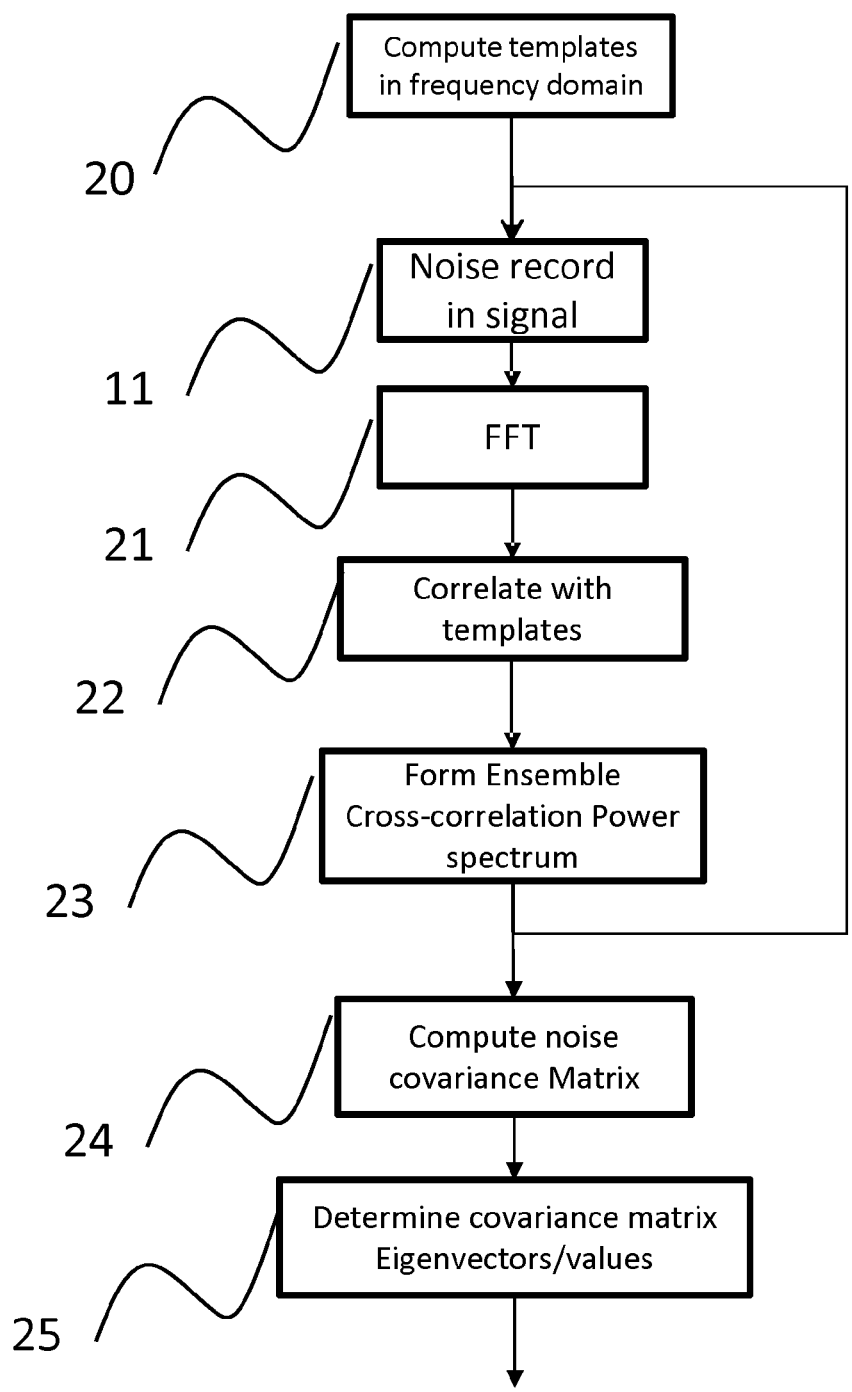
FIG. 7 is a flow diagram illustrating the steps for creation of a noise model.

Referring to FIG. 7, the templates 13 are computed in the frequency domain 20. A record of each noise region 11 is transformed into the frequency domain by Fast Fourier transform 21 and correlated 22 with each template by multiplication. The result is summed to form the mean cross-correlation spectrum 23. A mean noise co-variance matrix is derived 24 from the cross-correlation spectrum. The co-variance matrix is decomposed 25 into its eigenvectors and eigenvalues, thus forming a noise model 14.

Figure 8:
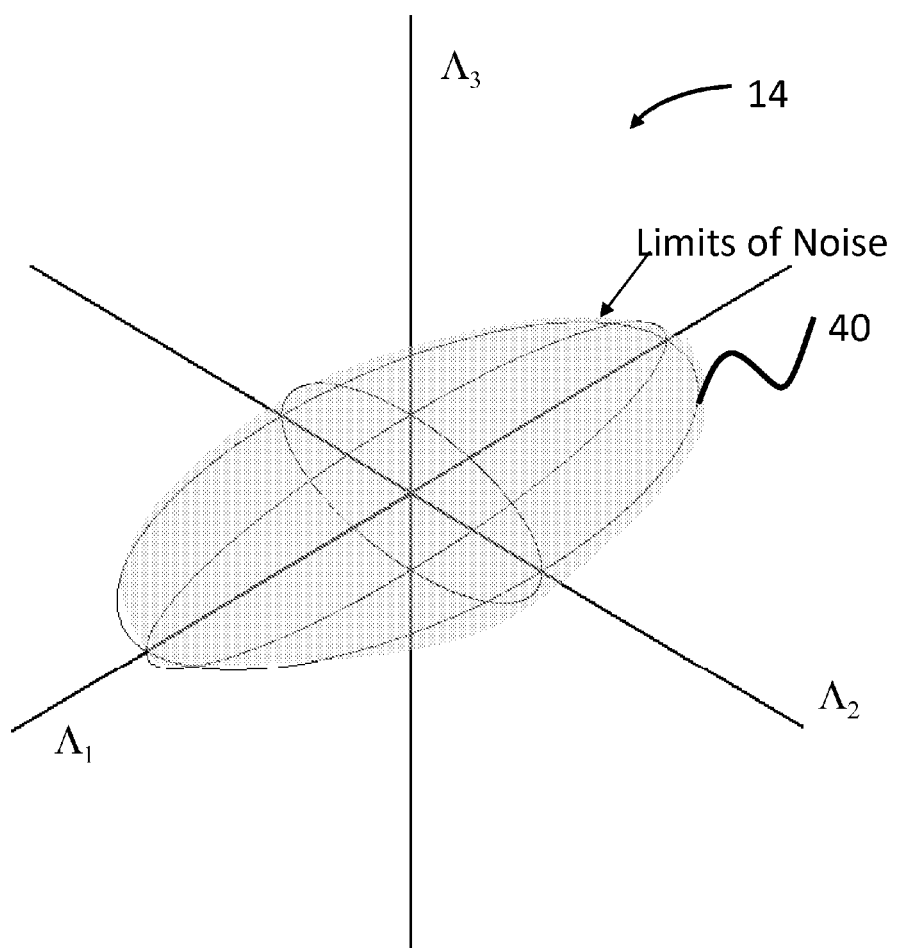
FIG. 8 is a graphical illustration of the noise model for three templates.

FIG. 8 illustrates a noise model for three templates only (because of the difficulties of showing high dimensional models). The three eigenvectors Λ1, Λ2, Λ3 are at rights angles, i.e. orthogonal. The limits of the noise model is shown by the shaded area 40 as defined by the eigenvalues.

Figure 9:
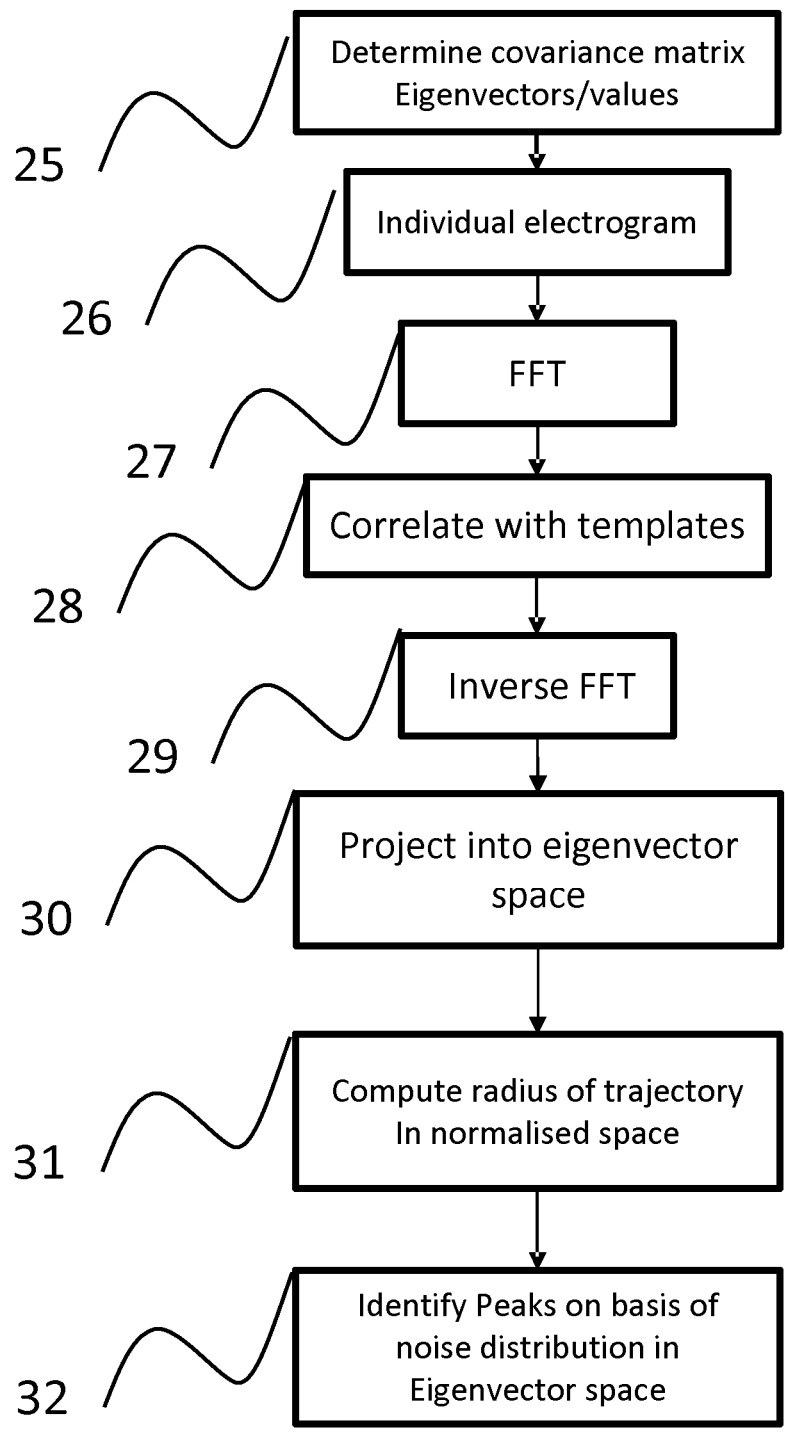
FIG. 9 is a flow diagram illustrated the steps for identification of potentials the noise model.

Referring to FIG. 9, every signal identification region 12 is processed individually. The individual signal portion 26 is transformed into the frequency domain 27 and correlated 28 with templates 13 and the result expressed 29 in the time domain. The resultant signal template correlation records are projected 30 into the eigenvector space of the noise model 14 as a trajectory.

Figure 10:
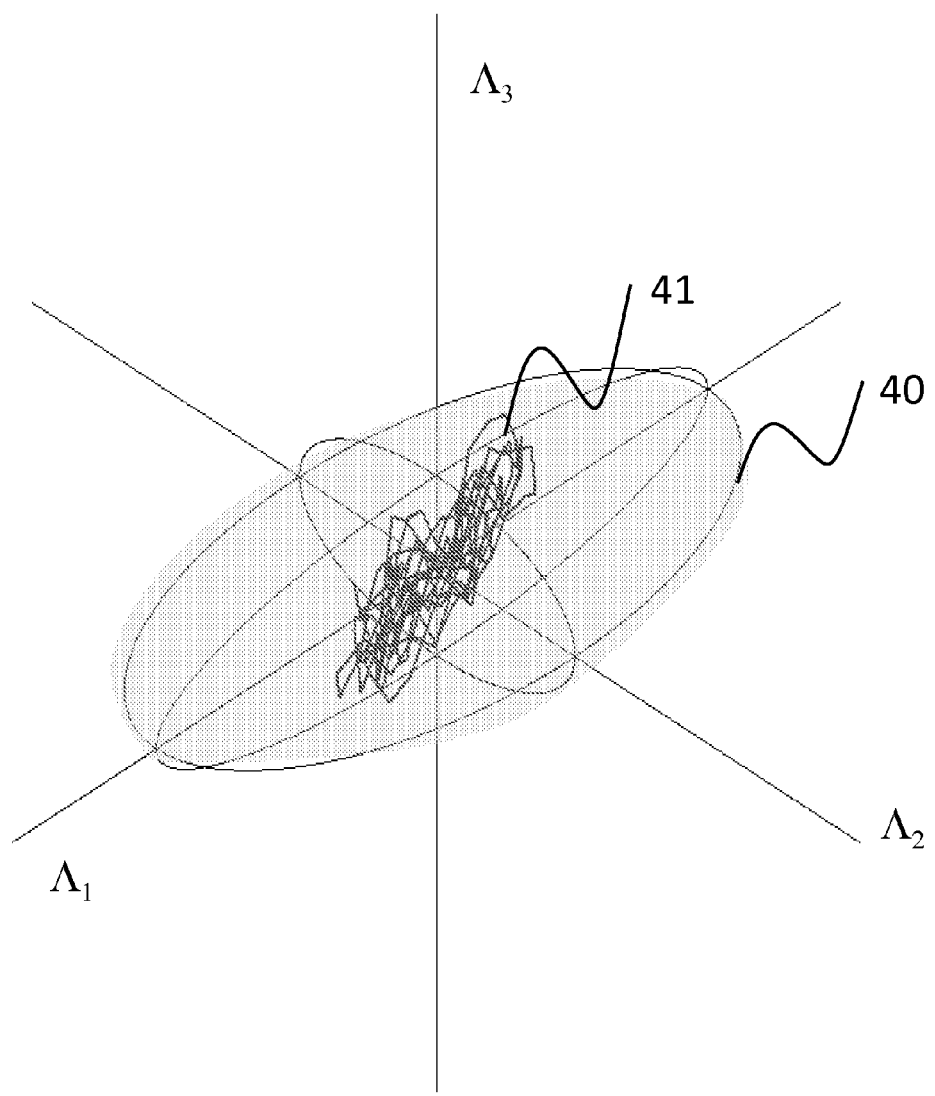
FIG. 10 is a graphical illustration of the noise model for three templates showing trajectory of one noise record within the noise model illustrating that it remains within the limits of the model.

FIG. 10 is an illustration of the trajectory 41 of a signal within region 11 illustrating that it remains within the limits 40 of the model 14 as defined by the eigenvectors/eigenvalues.

Figure 11:
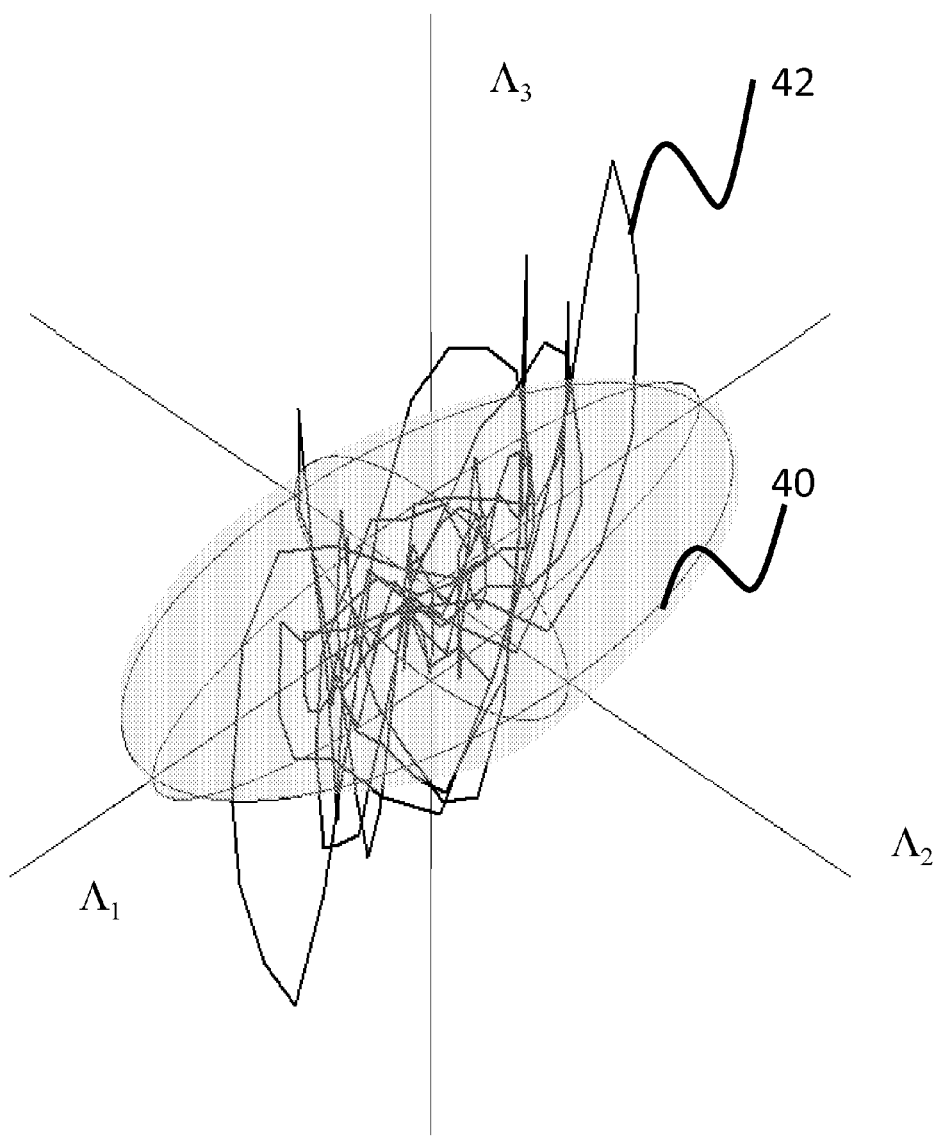
FIG. 11 a graphical illustration of the noise model for three templates showing a trajectory of a signal that is derived from a physiological signal.

FIG. 11 illustrates the trajectory 42 of a signal within the region 12 showing that it exceeds the limits 40 of the noise model 14 and thus is likely to be attributed to a physiological origin.

Figure 12:
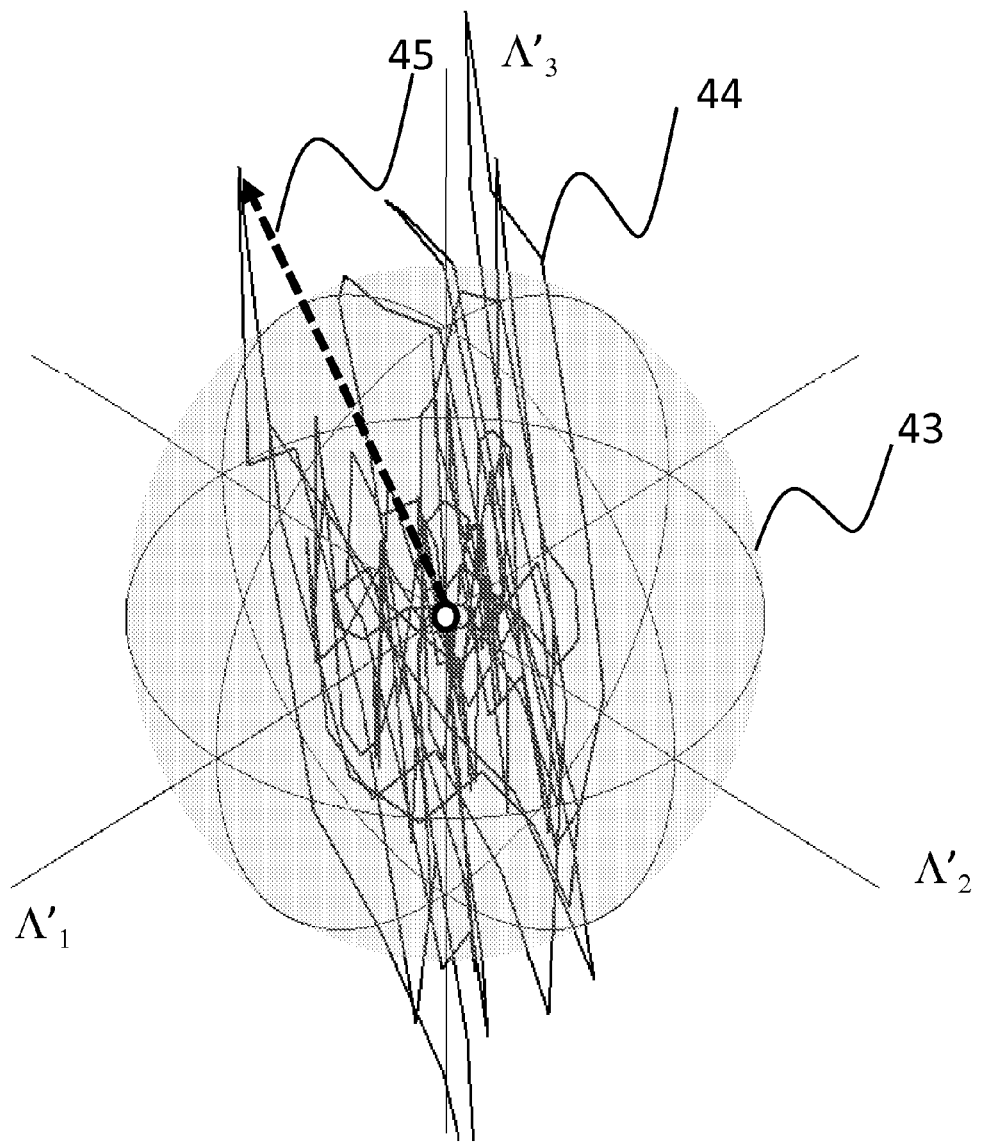
FIG. 12 is a graphically illustrates a normalized noise model for three templates.

A convenient method of determining whether the signal exceeds the noise is to reduce the trajectory to a single time domain signal. To achieve this, the resultant trajectory is normalized by division of each eigenvector by its eigenvalue so that the noise model becomes a spheroid 43 as illustrated in FIG. 12. The norm 45 of the trajectory vector in this space 44 is computed to give the one-dimensional time domain signal.

Any peak in the time domain signal that is above of the noise is considered to be physiologically significant.

Figure 13:
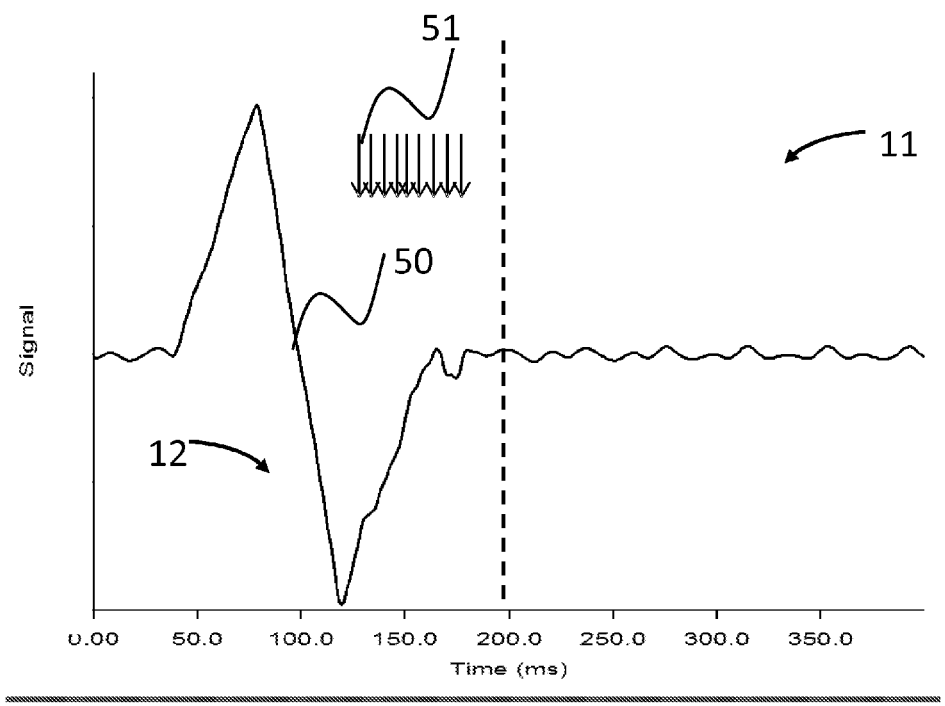
FIG. 13 illustrates a simulated electrogram to which noise and small potentials have been added.

FIG. 13 shows a portion of a simulated electrogram 50, corresponding to a single S1-S2 interval. Noise has been added to the electrogram together with small potentials expected from a physiological response. The small potentials have the same peak-to-peak amplitude of the noise; the positions of the small potentials are indicated by arrows 51.

Figure 14:
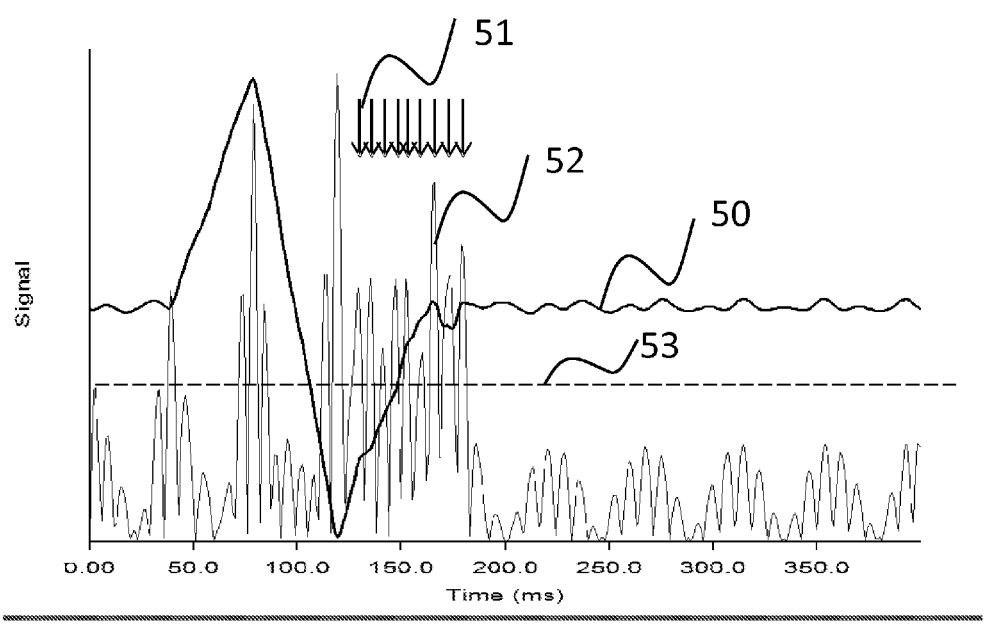
FIG. 14 illustrates the simulated electrogram of FIG. 13 with the time domain output signal of the model superimposed.

FIG. 14 shows the electrogram of FIG. 13 with a time domain signal output 52 derived using the method described above superimposed. The time domain signal output shows clear peaks that exceed the noise threshold 53 corresponding to the limit of the noise model, at the positions that the small potentials were inserted into the signal with a significant increase in signal to noise ratio.

The present subject matter can be embedded in a computer program product, which comprises all the features enabling the implementation of the methods described herein, and which—when loaded in a computer system—is able to carry out these methods. Computer program in the present context means any expression, in any language, code or notation, of a set of instructions intended to cause a system having an information processing capability to perform a particular function either directly or after either or both of the following a conversion to another language, code or, notation; and b reproduction in a different material form.

Each computer system may include, inter alia, one or more computers and at least a computer readable medium allowing a computer to read data, instructions, messages or message packets, and other computer readable information from the computer readable medium. The computer readable medium may include computer readable storage medium embodying non-volatile memory, such as read-only memory ROM, flash memory, disk drive memory, CD-ROM, and other permanent storage. Additionally, a computer medium may include volatile storage such as RAM, buffers, cache memory, and network circuits. Furthermore, in certain embodiments of the computer readable medium, other than a computer readable storage medium as discussed above, the computer readable medium may comprise computer readable information in a transitory state medium such as a network link and/or a network interface, including a wired network or a wireless network, that allow a computer to read such computer readable information.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

Although specific embodiments of the subject matter have been disclosed, those having ordinary skill in the art will understand that changes can be made to the specific embodiments without departing from the scope of the disclosed subject matter. The scope of the disclosure is not to be restricted, therefore, to the specific embodiments, and it is intended that the appended claims cover any and all such applications, modifications, and embodiments within the scope of the present disclosure.

The invention claimed is:

1. A method of analysing an electrogram to distinguish a physiological signal from noise; the method comprising:
    receiving a electrogram signal captured from a patient's heart, the electrogram signal including noise signals and physiological signals from the patient's heart, wherein:
        a first portion of the electrogram signal includes a noise signal absent a physiological signal, and
        a second portion of the electrogram signal includes a noise signal combined with a physiological signal;
    deriving a model of noise from the first portion of the electrogram signal by cross-correlation of the first portion of the electrogram signal with multiple templates that represent features of the physiological signal to produce a number of template correlated signals, the model of noise having limits within which a captured electrogram signal is defined as a noise signal and outside of which a captured electrogram signal is defined as a physiological signal;
    transforming, based on the model of noise, the second portion of the electrogram signal to a trajectory vector signal; and
    identifying the physiological signal in the second portion of the electrogram signal by identifying portions of the second portion of the electrogram signal that were transformed to portions of the trajectory vector signal that do not conform to the model of noise.

2. A method according to claim 1 wherein the model of noise is derived from multiple first portions of the electrogram signal that include a noise signal absent a physiological signal.

3. A method according to claim 1 comprising deriving a co-variance matrix from the template correlated signals for a plurality of first portions of the electrogram signal that each includes a noise signal absent a physiological signal.

4. A method according to claim 3 comprising deriving a mean co-variance matrix from the co-variance matrices derived for each of a plurality of first portions of the electrogram signal that each includes a noise signal absent a physiological signal.

5. A method according to claim 4 wherein the model of noise is expressed by deriving Eigenvectors and Eigen values from the mean co-variance matrix.

6. A method according to claim 1 comprising correlating the second portion of the electrogram signal with multiple templates that represent features of the physiological signal to produce a set of template correlated signals.

7. A method according to claim 1 comprising deriving a vector from a first time sample of each template correlated signal of the set; and further vectors from further time samples of each template correlated signal of the set.

8. A method according to claim 7 comprising representing the vectors as points in the model of noise by projecting each vector onto each eigenvector thereby representing the original signal as a trajectory in the model of noise.

9. A method according to claim 8 wherein a physiological signal is identified by determining points that lie outside the limits of the model of noise.

10. A method of analyzing a cardiac electrogram according to claim 1.

11. A method according to claim 1 comprising reducing the trajectory vector signal to a time domain signal, and outputting the time domain signal.

12. Apparatus for analysing a cardiac electrogram to distinguish a physiological signal from noise; the apparatus comprising:
    a signal generator to generate a pacing signal;
    an input electrode for applying the pacing signal to a patient's heart;
    a receiving electrode to receive a cardiac electrogram signal from the patient's heart, the cardiac electrogram signal received based on application of the pacing signal to the patient's heart, the cardiac electrogram signal including noise signals and physiological signals from the patient's heart, wherein:
        a first portion of the cardiac electrogram signal includes a noise signal absent a physiological signal, and
        a second portion of the cardiac electrogram signal includes a noise signal combined with a physiological signal;
    a memory store in which the received cardiac electrogram signal is stored; and
    a processor communicatively coupled to the memory store, the processor being responsive to executing computer instructions, to perform operations comprising:
        deriving a model of noise from the first portion of the cardiac electrogram signal by cross-correlation of the first portion of the electrogram signal with multiple templates that represent features of the physiological signal to produce a number of template correlated signals, the model of noise having limits within which a captured electrogram signal is defined as a noise signal and outside of which a captured electrogram signal is defined as a physiological signal;
        transforming, based on the model of noise, the second portion of the electrogram signal to a trajectory vector signal; and identifying the physiological signal in the second portion of the cardiac electrogram signal by identifying portions of the second portion of the cardiac electrogram signal that were transformed to portions of the trajectory vector signal that do not conform to the model of noise.

13. Apparatus according to claim 12 wherein the processor is responsive to executing computer instructions to derive the model of noise from multiple first portions of the cardiac electrogram signal that include a noise signal absent a physiological signal.

14. Apparatus according to claim 12 wherein the processor is responsive to executing computer instructions to derive a co-variance matrix from the template correlated signals for a plurality of first portions of the cardiac electrogram signal that each includes a noise signal absent a physiological signal.

15. Apparatus according to claim 14 wherein the processor is responsive to executing computer instructions to derive a mean co-variance matrix from the co-variance matrices derived for each of a plurality of first portions of the cardiac electrogram signal that each includes a noise signal absent a physiological signal.

16. Apparatus according to claim 15 wherein the processor is responsive to executing computer instructions to express the model by deriving Eigenvectors and Eigen values from the mean co-variance matrix.

17. Apparatus according to claim 12 wherein the processor is responsive to executing computer instructions to correlate the second portion of the cardiac electrogram signal with multiple templates that represent features of the physiological signal to produce a set of template correlated signals.

18. Apparatus according to claim 12 wherein the processor is responsive to executing computer instructions to derive a vector from a first time sample of each template correlated signal of the set; and further vectors from further time samples of each template correlated signal of the set.

19. Apparatus according to claim 18 wherein the processor is responsive to executing computer instructions to express the vectors as points in the model of noise by projecting each vector onto each Eigenvector thereby representing the original signal as a trajectory in the model of noise.

20. A method according to claim 11 comprising displaying the time domain signal overlaid with a noise threshold corresponding to the limits of the model of noise, portions of the time domain signal displayed above the noise threshold indicating they are physiologically significant.

* * * * *